United States Patent [19]

Nadelson

[11] 3,995,048
[45] Nov. 30, 1976

[54] ISOXAZOLYL BENZAMIDES USEFUL AS TRANQUILIZERS AND SLEEP-INDUCERS
[75] Inventor: Jeffrey Nadelson, Lake Parsippany, N.J.
[73] Assignee: Sandoz, Inc., E. Hanover, N.J.
[22] Filed: Oct. 20, 1975
[21] Appl. No.: 623,782

[52] U.S. Cl. .......................... 424/272; 260/307 F; 260/307 H; 260/325 PH; 260/558 A; 260/566 A
[51] Int. Cl.$^2$ ....................................... C07D 261/08
[58] Field of Search................ 260/307 H; 424/272

[56] References Cited
UNITED STATES PATENTS
3,578,673  5/1971  Bruson et al........................ 260/307

Primary Examiner—Raymond V. Rush
Attorney, Agent, or Firm—Gerald D. Sharkin; Robert S. Honor

[57] ABSTRACT

Substituted isoxazolyl benzamides, e.g., o-(3-trifluoromethyl-5-isoxazolyl)-N-methylbenzamide, are prepared by cyclizing a corresponding 1-hydroxy-1-[(2-hydroxyimino)-3-trifluoropropyl]-2-alkyl phthalimidine with a strong acid and are useful as minor tranquilizers and sleep inducers.

8 Claims, No Drawings

ISOXAZOLYL BENZAMIDES USEFUL AS TRANQUILIZERS AND SLEEP-INDUCERS

This invention relates to isoxazolyl benzamides which exhibit minor tranquilizer and sleep inducer activity. More particularly, it relates to substituted isoxazolyl benzamides, intermediates thereof, and to processes for their preparation.

The compounds of this invention may be represented by the following structural formula

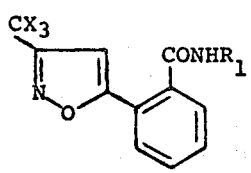

where
X represents hydrogen or fluoro, and
$R_1$ represents straight chain lower alkyl, i.e. straight chain lower alkyl having 1 to 4 carbon atoms, e.g. methyl, ethyl, propyl and the like.

The compounds of formula (I) are prepared according to the following reaction scheme:

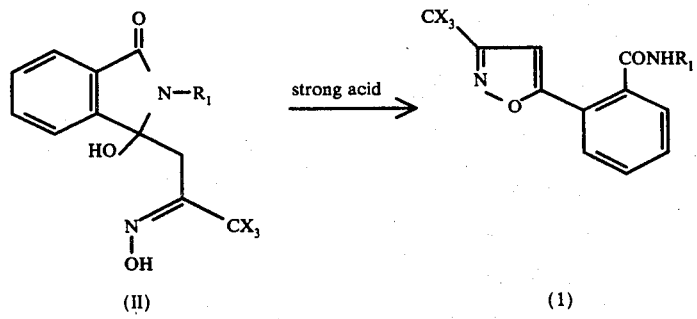

where
X and $R_1$ are as defined above.

The compounds of formula (I) are prepared by cyclizing a compound of the formula (II) with a strong nonaqueous acid such as concentrated sulfuric acid or polyphosphoric acid, the latter being especially preferred. Although an inert solvent can be used such as diethyl ether, tetrahydrofuran, dioxane, an aliphatic hydrocarbon, aromatic hydrocarbon, or halogenated hydrocarbon, it is preferred that the reaction be carried out in excess of the acid employed, e.g. polyphosphoric acid. The temperature of the reaction is not critical, but it is preferred that the reaction be carried out at a temperature between about 100° to 180° C., preferably from about 130° to 150° C. The reaction may be run from 30 minutes to 8 hours, preferably from about 30 minutes to 2 hours. The product is recovered by conventional techniques, e.g., crystallization followed by trituration.

The compounds of formula (II) are prepared according to the following reaction scheme:

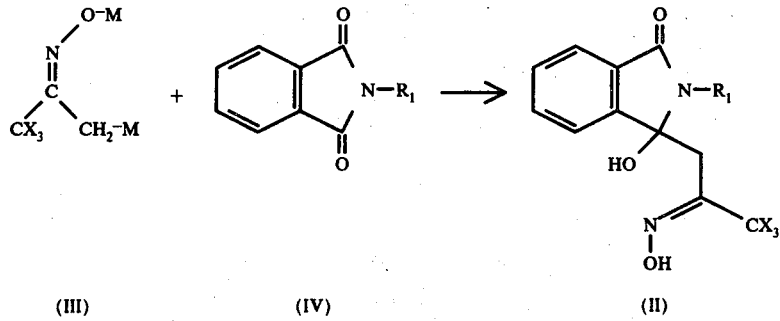

where
M is lithium, and
X and $R_1$ are as defined above.

The compounds of formula (II) are prepared by reacting a compound of formula (III) with a compound of formula (IV) in an inert solvent. The particular inert solvent used is not critical, but it is preferred that the reaction be carried out in the presence of an ether, such as tetrahydrofuran, dioxane, diethyl ether and the like or an aliphatic hydrocarbon such as heptane, hexane and the like, preferably tetrahydrofuran. The temperature of the reaction is not critical, but it is preferred that the reaction be carried out at a temperature between about 0° to 80° C., preferably at room temperature. The reaction may be run from 1 to 12 hours, preferably from about 1½ to 3 hours. The resulting adduct of the compounds of formulae (III) and (IV) is hydrolyzed to the compounds of formula (II) using conventional techniques, e.g. by use of ammonium chloride solution. The product is recovered using conventional techniques, e.g., evaporation and recrystallization.

The compounds of formula (III) are prepared according to the following reaction scheme:

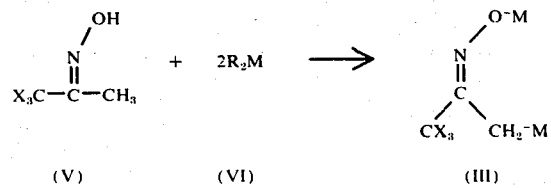

where
$R_2$ is lower alkyl having 1 to 4 carbon atoms, and
X and M are as defined above.

The compounds of formula (III) are prepared by reacting a compound of the formula (V) with a compound of the formula (VI) employing conventional techniques.

It is to be noted that the compounds of formula (II) also exist in the following tautomeric forms and said tautomeric forms are also included within this invention.

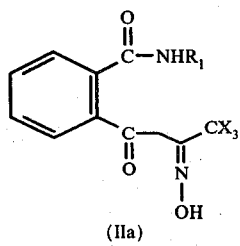 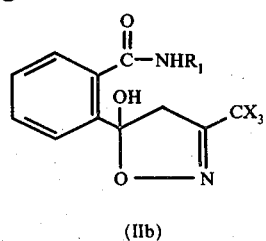

(IIa)  (IIb)

where

R₁ and X are as defined above.

For the sake of simplicity, the compounds of formula (II) will be referred to in the Specification as compounds (II) but it should be understood that structures (IIa) and (IIb) are also an aspect of the present invention.

Many of the compounds of formula (III), (IV) and (V) are known and may be prepared by methods described in the literature. The compounds of formulae (III), (IV) and (V) not specifically disclosed may be prepared by analogous methods from known starting materials.

The compounds of formula (I) are useful because they possess pharmacological activity. In particular, the compounds are useful as central nervous system depressants, especially as sleep inducers and minor tranquilizers, as indicated by (1) their ability to produce docility in behavior tests in mice given 20 to 50 mg/kg of animal body weight, i.p. of the test compound according to the 30-word adjective check sheet system basically as described by Irwin S. Gordon (Research Conference, Medicinal Chemistry, 1959) and Chen (Symposium on Sedative and Hypnotic Drugs, Williams and Wilkins, 1954); (2) by their ability to antagonize chronic convulsions and death in mice given 4 to 50 mg/kg i.p. of the test compound followed by 50 mg/kg i.p. of N-sulfamoyl-azepine; (3) by the hexobarbital reinduction method of Winger (J. Pharmacol. and Exp. Therap., 94, 7–11, 1948), in which the reinduction of anesthesia after recovery from hexobarbital induced anesthesia is used to determine sedative-hypnotic activity in mice given 70 mg/kg of animal body weight, i.p. of hexobarbital followed immediately after the mice regain their righting reflexes by 10 to 50 mg/kg of animal body weight, i.p. of the test compound; and (4) by scoring for loss of righting reflex according to the method of Reed-Muench (American Journal of Hygiene, 27:493–497, 1938) in which mice are administered 12.5 mg/kg i.p. thioridazine, immediately after which test compound is administered at dosages of 13.5 to 50 mg/kg in a volume of 0.1 ml/10 g. body weight. Thirty minutes after dosing, the mice are scored for loss of righting reflex.

For such usage, the compounds may be administered orally or parenterally as such or admixed with conventional pharmaceutical carriers.

The dosage of active ingredient employed for minor tranquilizer use may vary depending on the severity of the condition being treated. However, in general, satisfactory results are obtained when a compound of formula (I) is administered at a daily dosage of from about 4 milligrams to about 50 milligrams per kilogram of animal body weight p.o., preferably given in divided doses 2 to 4 times a day, or in sustained release form. For most larger mammals (e.g., primates), the total daily dosage is from about 250 milligrams to about 3000 milligrams. Dosage forms suitable for internal use comprise from about 60 to about 1500 milligrams of active compound in intimate admixture with a solid or liquid pharmaceutically acceptable carrier or diluent.

The dosage of active ingredient employed for sleep inducer use may vary depending on the severity of the condition being treated. However, in general, satisfactory results are obtained when a compound of the formula (I) is administered at a daily dosage of from about 10 milligrams to about 50 milligrams per kilogram of animal body weight p.o., typically given in a single dose at bedtime. For most larger mammals, the total daily dosage is from about 100 milligrams to about 2000 milligrams, preferably at bedtime in a single dose, and dosage forms suitable for internal administration comprise from about 25 to 1000 milligrams of the compound in admixture with a solid or liquid pharmaceutical carrier or diluent. The preferred pharmaceutical compositions from the standpoint of preparation and ease of administration are solid compositions, particularly hard-filled capsules and tablets.

EXAMPLE I.

1-Hydroxy-1-[(2-hydroxyimino)propyl]-2-methyl-phthalimidine

A solution of 24.8 g. (0.34 mole) acetone oxime in 500 ml. tetrahydrofuran is cooled to 0° C. and there is added dropwise 468 ml. n-butyllithium in hexane (0.075 mole) with the temperature not exceeding +5° C. during the addition. After the addition is complete, the mixture is stirred for 2½ hours at 0° C. and then warmed to 10° C., and there is added dropwise a solution of 59.6 g. (0.37 mole) N-methyl phthalimide in 330 ml. tetrahydrofuran maintaining the temperature below 30° C. After the addition is complete, the mixture is stirred for 1½ hours at 0° to 10° C. and quenched by the addition of saturated ammonium chloride. The layers are separated and the organic phase is washed with ammonium chloride solution, dried and evaporated in vacuo. The solid residue is triturated with ether, filtered and recrystallized from methanol/ether to give 1-hydroxy-1-[(2-hydroxyimino)propyl]-2-methyl-phthalimidine; m.p. 143° to 145° C.

EXAMPLE II.

o-(3-methyl-5-isoxazolyl)-N-methyl benzamide

A mixture of 50.5 g. (0.234 mole) 1-hydroxy-1-[(2-hydroxyimino)propyl]-2-methyl-phthalimidine and 750 g. of polyphosphoric acid is heated at 140° C. for ½ hours. The mixture is poured onto ice and extracted three times with 600 ml. of methylene chloride. The methylene chloride is washed with brine, decolorized, dried over magnesium sulfate, filtered and evaporated in vacuo. The residue is crystallized from ether and the resulting solid triturated with cold methylene chloride to give o-(3-methyl-5-isoxazolyl)-N-methyl benzamide; m.p. 120.5° to 122.5° C.

The o-(3-methyl-5-isoxazolyl)-N-methyl benzamide of this example is an effective sleep inducer when orally administered to an animal in need of said treatment at a dosage of 200 mg. just before bedtime. The o-(3-methyl-5-isoxazolyl)-N-methyl benzamide of this example is also an effective minor tranquilizer when orally administered to an animal in need of said treatment at a dosage of 100 mg. 2 to 4 times per day.

EXAMPLE III.

Following the procedure of Example I, and using in place of acetone oxime, 43.2 g. (0.34 mole) of trifluoromethyl acetone oxime, there is obtained by trituration with cold methylene chloride 1-hydroxy-1-[(2-hydroxyimino)-3-trifluoropropyl]-2-methyl-phthalimidine; m.p. 168° to 170° C.

EXAMPLE IV.

Following the procedure of Example II, and using in place of 1-hydroxy-1-[(2-hydroxyimino)propyl]-2-methyl-phthalimidine, 67.5 g. (0.234 mole) of 1-hydroxy-1-[(2-hydroxyimino)-3-trifluoropropyl]-2-methyl-phthalimidine, there is obtained o-(3-trifluoromethyl-5-isoxazolyl)-N-methyl benzamide; m.p. 134° to 135° C.

What is claimed is:
1. A compound of the formula

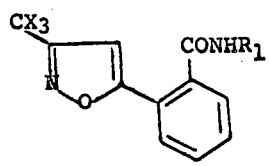

where
X represents hydrogen or fluoro, and
$R_1$ represents straight chain lower alkyl having 1 to 4 carbon atoms.
2. A compound of the formula

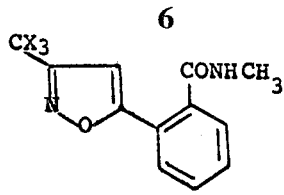

where
X is as defined in claim 1.
3. The compound of claim 2 which is o-(3-methyl-5-isoxazolyl)-N-methyl benzamide.
4. The compound of claim 2 which is o-(3-trifluoromethyl-5-isoxazolyl)-N-methyl benzamide.
5. The method of treating insomnia which comprises administering to a mammal in need of said treatment an effective amount of a compound according to claim 2.
6. The method of treating anxiety, which comprises administering to a mammal in need of said treatment an effective amount of a compound according to claim 2.
7. A pharmaceutical composition for use in the treatment of insomnia comprising from about 25 milligrams to about 1000 milligrams of a compound of claim 2 and a pharmaceutically acceptable diluent or carrier therefor.
8. A pharmaceutical composition for use in the treatment of anxiety comprising from about 60 milligrams to about 1500 milligrams of a compound of claim 2 and a pharmaceutically acceptable diluent or carrier therefor.

* * * * *